(12) United States Patent
Myklebust et al.

(10) Patent No.: US 6,807,442 B1
(45) Date of Patent: Oct. 19, 2004

(54) SYSTEM FOR REDUCING SIGNAL DISTURBANCES IN ECG, WHICH DISTURBANCES ARE CAUSED BY CARDIO-PULMONARY RESUSCITATION

(75) Inventors: Helge Myklebust, Stavanger (NO); Trygve Eftestøl, Forus (NO); Bjørn Terje Holten, Hafrsfjord (NO); Sven Ole Aase, Stavanger (NO)

(73) Assignee: Laerdal Medical AS, Stavanger (NO)

( * ) Notice: Subject to any disclaimer, the term of this patent is extended or adjusted under 35 U.S.C. 154(b) by 63 days.

(21) Appl. No.: 09/645,443

(22) Filed: Aug. 25, 2000

(30) Foreign Application Priority Data

Aug. 27, 1999  (NO) .......................................... 1999 4153

(51) Int. Cl.[7] .............................................. A61B 5/0402
(52) U.S. Cl. .......................................... 600/509; 607/5
(58) Field of Search .............................. 600/509; 607/5

(56) References Cited

U.S. PATENT DOCUMENTS

| | | | |
|---|---|---|---|
| 4,991,587 A | | 2/1991 | Blakeley et al. |
| 5,025,794 A | * | 6/1991 | Albert et al. ................ 128/696 |
| 5,247,939 A | | 9/1993 | Sjoquist et al. |
| 5,376,104 A | * | 12/1994 | Sakai et al. ..................... 607/5 |
| 5,458,123 A | * | 10/1995 | Unger ......................... 128/696 |
| 5,474,574 A | | 12/1995 | Payne et al. |
| 5,812,678 A | * | 9/1998 | Scalise et al. ................. 381/67 |
| 5,964,701 A | * | 10/1999 | Asada et al. ................. 600/300 |
| 6,148,233 A | * | 11/2000 | Owen et al. .................... 607/5 |
| 6,155,257 A | * | 12/2000 | Lurie et al. ............. 128/204.23 |
| 6,155,976 A | * | 12/2000 | Sackner et al. .............. 600/300 |
| 6,273,728 B1 | * | 8/2001 | van Meurs et al. .......... 434/268 |
| 6,306,107 B1 | | 10/2001 | Myklebust et al. |
| 6,351,671 B1 | | 2/2002 | Myklebust et al. |
| 6,390,996 B1 | * | 5/2002 | Halperin et al. ............... 601/41 |

OTHER PUBLICATIONS

Aase et al., "CPR Artifact Removal from Human ECG Using Optimal Multichannel Filtering", IEEE Transactions on Biomedical Engineering 47(11):1440–1449, Nov. 2000.
Aase et al., "Compression Depth Estimation for CPR Quality Assessment Using DSP on Accelerometer Signals", IEEE Transactions on Biomedical Engineering 49(3):263–268, Mar. 2002.
"Advisory Statements of the International Liaison Committee on Resuscitation", Circulation, p. 2181, 1997.
Dickey, et al., "The Accuracy of Decision–Making of a Semi–Automatic Defibrillator During Cardiac Arrest", Eur. Heart J. 13(5):608–615, May 1992.
Eftestol et al., "Effects of Interrupting Precordial Compressions on the Calculated Probability of Defibrillation Success During Out–of Hospital Cardiac Arrest", Accepted for publication 2002.
Geddes et al., "Principles of Applied Biomedical Instrumentation", Third Ed., pp. 370–373, ©1989.

(List continued on next page.)

Primary Examiner—Jeffrey R. Jastrzab
Assistant Examiner—Frances P. Oropeza
(74) Attorney, Agent, or Firm—Nixon & Vanderhye P.C.

(57) ABSTRACT

A system for reducing signal disturbances in ECG, which disturbances are caused by cardio-pulmonary resuscitation (CPR). The system includes a measuring device for measuring one or more signals derived from parameters such as compression depth, lung inflation etc. as a result of CPR. The parameter signals form one or more reference signals that correlate with the signal disturbances. One or more adaptive filters filter the signals out from the signal that constitutes the ECG signals so as to remove disturbances caused by CPR.

19 Claims, 5 Drawing Sheets

OTHER PUBLICATIONS

"Guidelines 2000 for Cardiopulmonary Resuscitation and Emergency Cardiovascular Care", Int'l Consensus on Science, American Heart Association/European Resuscitation Council, pp. 164–168, Aug, 2000.

Husoy et al. "Removal of Cardiopulmonary Resuscitation Artifacts from Human ECG Using an Efficient Matching Pursuit–like Algorithm", IEEE Transactions on Biomedical Engineering, (Accepted for publication), vol. XX, No. Y, 2002.

Kerber, et al., "Automatic External Defibrillators for Public Access Defibrillation: Recommendations for Specifying . . . Enhancing Safety", Circulation, 95:1677–1682, 1997.

Langhelle et al., "Reducing CPR Artefacts in Ventricular Fibrillation in Vitro", Resuscitation 48:279–291, 2001.

Sato et al, "Adverse effects of interrupting precordial compression during cardiopulmonary resuscitation", *Crit Care Med*, 1997, vol. 25, pp. 733–736.

"Advisory Statements of the International Liaison Committee on Resuscitation", *Ilcor Advisory Statement*, American Heart Association, 1997, pp. 2172–2210.

"Guidelines for Cardiopulmonary Resuscitation and Emergency Cardiac Care", Journal of the American Medical Association, Oct. 28, 1992, vol. 268, No. 16, pp. 2171–2302.

Shen Luo et al; "Experimental study: brachial motion artifact reduction in the ECG"; Computers in Cardiology 1995; (CAT. No. 95CH35874), Vienna, Austria, Sept. 10–13, 1995; pp. 33–35.

Provaznik I et al; "Adaptive recurrent system for noise cancellation and arrhythmia detection"; Proceedings of the 16th Annual International Conference of the IEEE Engineering in Medicine and Biology Society. Engineering Advances: New Opportunities for Biomedical Engineers; (CAT No. 94CH3474–4); Proceedings of 16th Annual International Conference; 1994; pp. 270–1271, vol. 2.

Thakor N V et al; "Applications of adaptive filtering to ECG analysis; noise cancellation and arrhythmia detection" IEEE Transactions on Biomedical Engineering, Aug. 1991; vol. 38, No. 8, pp. 785–794.

Aase et al., "CPR Artifact Removal from Human ECG Using Optimal Multichannel Filtering", IEEE Transactions on Biomedical Engineering, vol. 47, No. 11, Nov. 2000, pp. 1440–1449.

Fitzgibbon et al., "Determination of the Noise Source in the Electrocardiogram during Cardiopulmonary Resuscitation", Crit Care Med 2002, vol. 30, No. 4 (Suppl.), pp. S148–S153.

Gruben et al., "System for Mechanical Measurements during Cardiopulmonary Resuscitation in Humans", IEEE Transactions on Biomedical Engineering, vol. 37, No. 2, Feb. 1990, pp. 204–210.

Langhelle et al., "Reducing CPR Artefacts in Ventricular Fibrillation in Vitro", Resuscitation 48, 2001, pp. 279–291.

\* cited by examiner

SYSTEM FOR REDUCING SIGNAL DISTURBANCES IN ECG, WHICH DISTURBANCES ARE CAUSED BY CARDIO-PULMONARY RESUSCITATION

BACKGROUND OF THE INVENTION

1. Field of the Invention

The present invention regards a system for reducing signal disturbances in electrocardiogram (ECG), which disturbances are caused by cardio-pulmonary resuscitation.

2. Description of Related Art

The three primary means of treating sudden cardiac death are cardio-pulmonary resuscitation (CPR), defibrillator shocks and medication, cf. the publications [1] "Advisory Statements of the International Liaison committee on Resuscitation (ILCOR). Circulation 1997;95:2172–2184, and [2]"Guidelines for Cardiopulmonary Resuscitation and Emergency Cardiac Care". Journal of the American Medical Association, Oct. 28, 1992, Vol. 268 No 16: 2171–2302.

The normal course of action in the case of sudden cardiac death and a resuscitation attempt is to first administer CPR until the defibrillator arrives, and then alternate between shocks from the defibrillator and CPR until the patient has a distinct pulse or until an ALS team arrives (ALS= Advanced Life Support). Then, securing of the respiratory passages and use of medication will be included together with the alternating use of a defibrillator and CPR. The first step towards resuscitation is to restore spontaneous heart activity and sufficient blood pressure. This is often termed ROSC (Return of Spontaneous Circulation).

The protocol that guides the defibrillator-CPR treatment states that, upon arrival of the defibrillator, three shocks should be administered initially, followed by 1 minute of CPR, then three new shocks and so on [1]. In order to administer a shock, the ECG must first be measured, analysed and classified as "Treat" or "Notreat". Defibrillators of the automatic or semi-automatic type will do this automatically, and this type of defibrillator is often called an AED (Automated External Defibrillator). The part of the software that performs this classification is usually described as the VF algorithm. After concluding the rhythm, the defibrillator will ready itself for shock delivery, report its readiness to deliver shocks, and wait for the user to operate the shock button. This procedure takes time, and it takes about one minute to administer three shocks. This is time during which the patient does not receive CPR, and during which vital organs, especially the brain, is damaged further due to the lack of blood supply [1].

Furthermore, this procedure entails the shock being delivered approximately 20 seconds after the CPR has been concluded. Animal experiments have shown that the probability of achieving ROSC decreases rapidly with time from conclusion of the CPR. The best chance of achieving ROSC is through delivering the shock without delay following CPR, cf. the publication [3] by Sato Y, Weil M H, Sun S et al., titled "Adverse effects of interrupting precordial compressions during cardiopulmonary resuscitation" in Crit Care Med 1997;25:733–736.

Performance of CPR has a disturbing effect on the ECG signals. The disturbances take the form of rhythmic signals, and occur simultaneously with heart compressions or inflations. As heart compressions are administered at a rate of 80–100 per minute, these rhythmic disturbances will generally cause the VF algorithm to draw incorrect conclusions in those cases where the rhythm is VF (ventricle fibrillation) or VT (ventricle tachyardia). This is caused by the algorithm interpreting the rhythmic disturbances as a pumping rhythm; i.e. there is no requirement for defibrillator shocks. It is therefore normal procedure to use the VF algorithm only after CPR has been concluded, cf. publication [1].

BRIEF SUMMARY OF THE INVENTION

The present invention regards a system that reduces the disturbances in the ECG during heart compression though use of adaptive digital filtering as stated in the introduction. The following advantages are derived from the invention.

As the VF algorithm can conclude while CPR is being performed, this will lead to less time being used for shock delivery, thereby leaving more time for CPR.

For the same reason, the shock may be delivered sooner following the conclusion of the CPR, something that will directly increase the probability of ROSC.

It becomes possible to perform signal analysis of VF for other purposes than classification. A useful possibility is to measure the characteristics of the heart that may indicate how effective the CPR is.

BRIEF DESCRIPTION OF THE DRAWINGS

In the following, the invention will be described in greater detail with reference to the drawings, in which.

DETAILED DESCRIPTION OF EXEMPLARY EMBODIMENTS OF THE INVENTION

Figure 1:
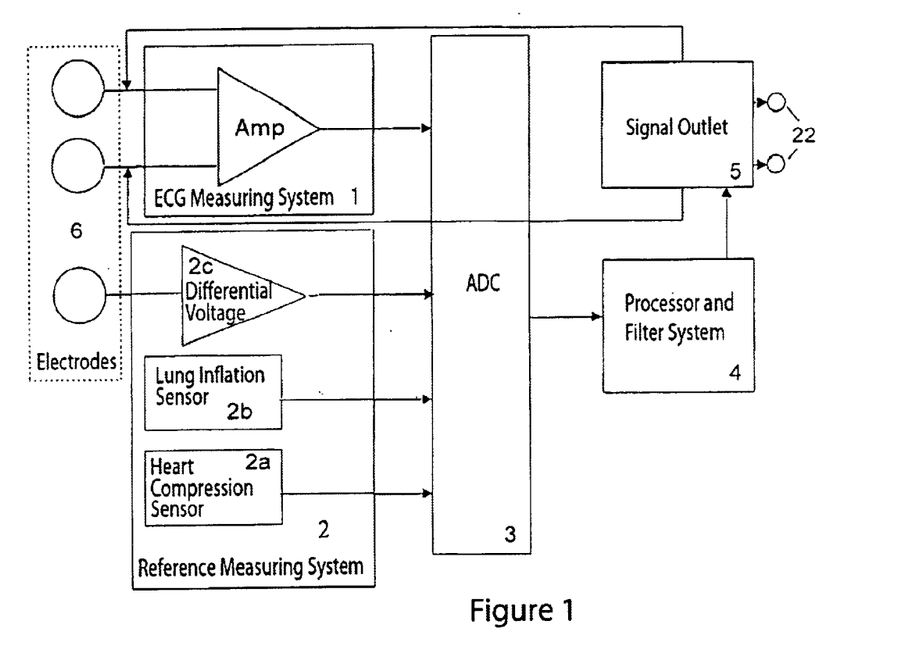
FIG. 1 schematically shows a circuit diagram of the system according to the invention.

The system components may be split into the ECG measuring system, indicated by reference number 1 in FIG. 1, and, as shown further in FIG. 1, reference measuring system 2, analogue to digital converter (ADC) 3, processor and filter system 4, signal outlet 5 and electrodes 6.

The system may be used:

a) Integrated into a defibrillator.

b) As a functional unit connected to an automatic CPR machine.

c) As a self-contained system that can deliver a filtered ECG to a stand-alone defibrillator.

The following describes the above system components in greater detail:

ECG Measuring System 1

Figure 5A:
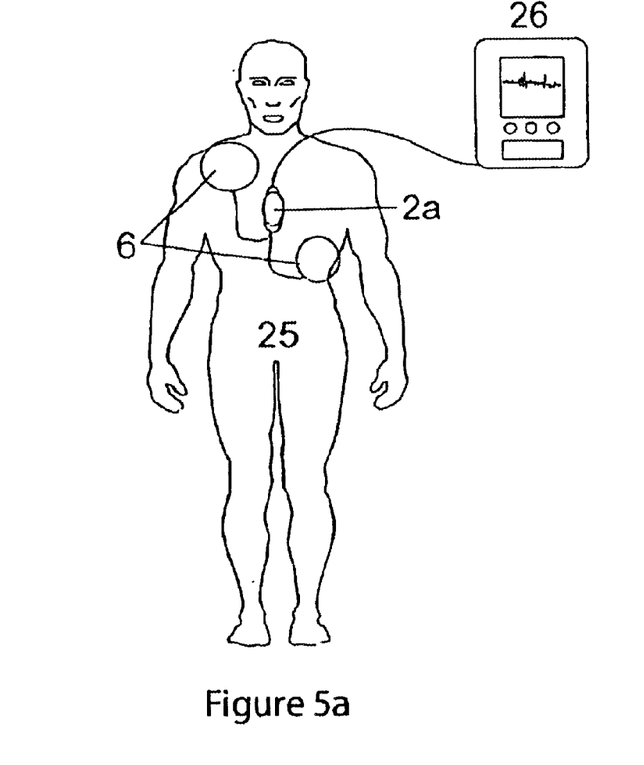
FIG. 5a shows an application where the system is integrated into a defibrillator.
Figure 5B:
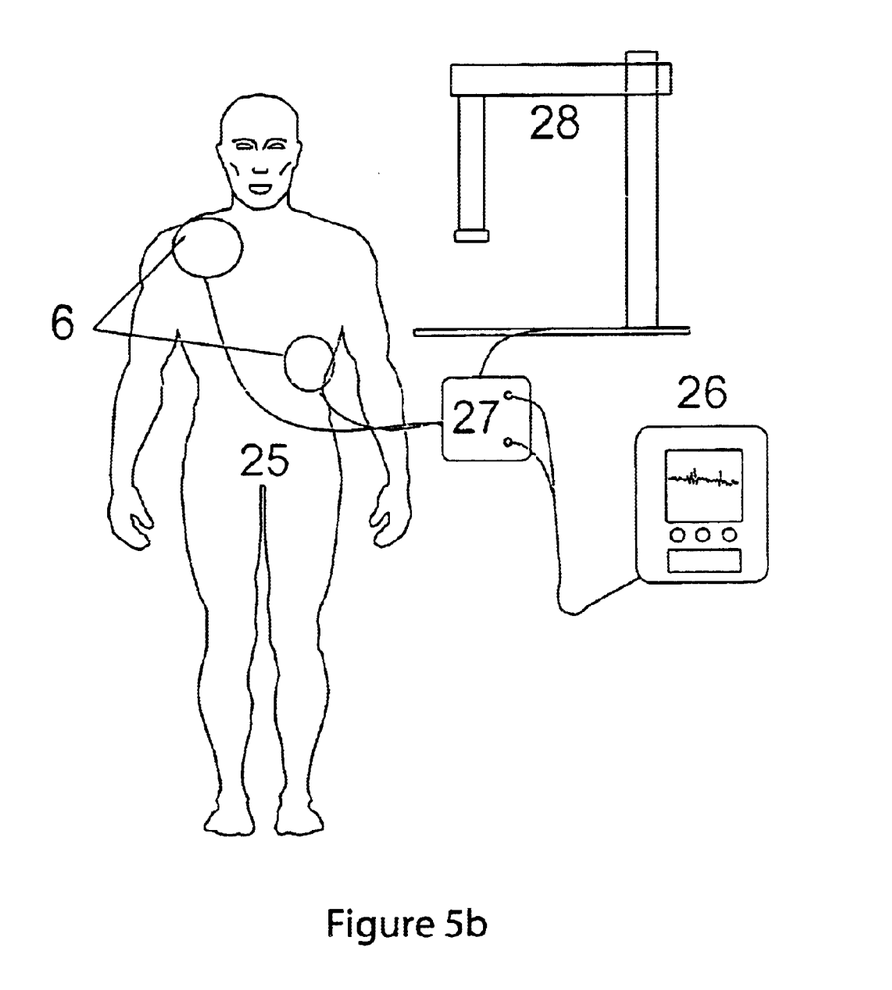
FIG. 5b shows an application where the system forms a functional unit connected to an automatic CPR machine.

The ECG measuring system 1 consists of at least two electrodes 6 connected to the patient 25, cf. FIGS. 5a–5b, a network that protects the inlet against overvoltage, as well as one or more buffers/amplifiers that deliver the result of the measurement to the ADC 3. In a defibrillator, this is normally part of the standard design.

Reference Measuring System 2

The reference measuring system 2 consists of a sensor and signal processing for estimating the depth of the heart compressions 2a; possibly also a sensor and signal processing for estimating the lung inflations 2b and possibly also a sensor and signal processing for estimating the differential voltage between the measuring system and the patient 2c. Several techniques may be used for the estimation of compression depth: In the case of CPR, the impedance between two electrodes placed at standard defibrillation positions will be altered. By an approximately constant alternating current being impressed between the electrodes, the impedance change will be represented by a voltage change measured between the electrodes. The change in voltage expresses both heart compression and lung inflation, by the current path between the electrodes changing during CPR.

Figure 2A:
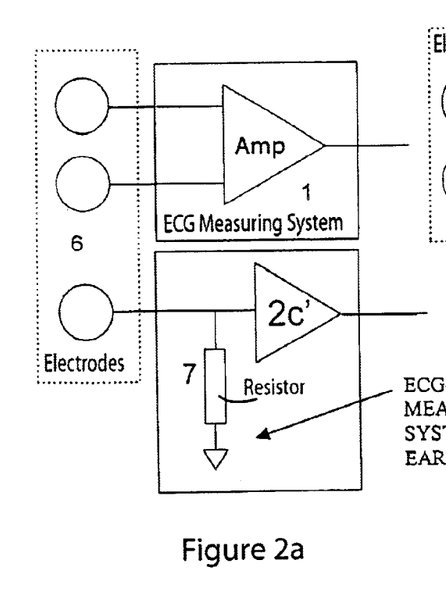
FIG. 2a shows the basic circuit arrangement for measuring the voltage between the patient and the measuring system when using a separate earth electrode

Alternatively, an accelerometer that follows the movements of the chest during heart compression via signal processing and conversion will express the depth of the heart compression. Alternatively, a linear position transmitter connected to e.g. an automatic CPR machine 28 will indicate the depth of the compression. Likewise, a sensor for measuring air volume or a sensor for measuring respiratory passage pressure may represent a signal for lung inflation. This type of signal is normally available from an automatic CPR machine 28, cf. FIG. 5b. The sensor for estimating the differential voltage between the measuring system and the patient may be a resistor and an amplifier. The connection may be effected in several ways, depending on the topology of the ECG amplifier. FIG. 2a shows the connection schematic with an earth electrode. Here, the charge equalisation between the patient and the measuring system will primarily go via the resistor 7, the voltage of which is measured by the amplifier 2c'. This voltage will then be correlated with the signal disturbances that are caused by charge equalisation and imbalance in the impedance between the patient 25 and each of the electrodes 6.

Figure 2B:
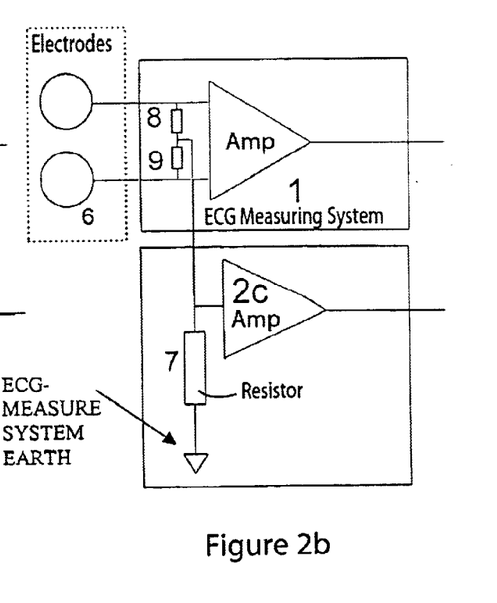
FIG. 2b shows the basic circuit arrangement for measuring the voltage between the patient and the measuring system when not using a separate earth electrode

FIG. 2b shows the connection schematic in the case where the patient is not connected to earth. The charge equalisation between the patient and the measuring system will primarily go via the resistor 7, and then distribute via the resistors 8 and 9 to the patient 25 via electrodes 6. The voltage across the resistor 7 will then be correlated with the signal disturbances that are caused by charge equalisation and imbalance in the impedance between the patient 25 and each of the electrodes 6.

ADC 3

ADC 3 converts each of the analogue channels to a digital channel that can be read by the processor and filter system 4. In a defibrillator 26, ADC3 normally forms part of the standard design.

Processor and Filter System 4

The processor and filter system 4 receives the raw data from the ADC 3 and sends the filtered data onwards. Adaptive digital filtering is used as the filtering method, cf. FIG. 3. This method has the special feature of being able to reduce disturbances that have a frequency distribution that overlaps the frequency distribution of the signal being disturbed. Furthermore, the method will adapt to changes in the signal disturbance with time. Disturbances that are caused by CPR will be of such a nature.

Figure 3:
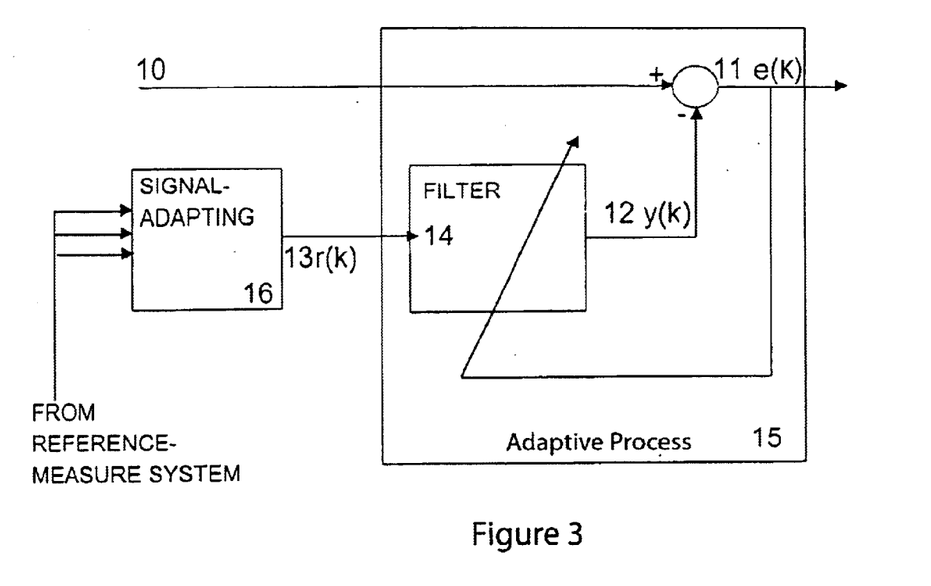
FIG. 3 shows the principle of the course of the signal in a digital adaptive filter.

The main components in an adaptive digital filter are:

- The primary signal 10 is ECG with signal disturbances in digital form, and may be described through the formula:

$$d(k)=s(k)+n(k)$$

in which s(k) is the desired signal (pure ECG) and n(k) is the disturbance.

- The output signal e(k), indicated by reference number 11 in FIG. 3, is an estimate of the initial ECG signal after filtering.

- The output signal y(k), indicated by reference number 12 in FIG. 3, is an estimate of the initial signal disturbance.

- The reference signal r(k) is normally described as the filter input signal, and is indicated by reference number 13 in FIG. 3. r(k) correlates with the disturbance.

- Digital filter 14, typically a FIR filter with a number of taps, preferably 9.

- Adaptive process 15, methodology to adjust the parameters of the filter in such a way that the estimate e(k) converges to s(k), preferably of the type Conjugate Gradient, (CG).

- The methodology in a digital adaptive filter is as follows: The expectancy value of the square of the output signal e(n) is minimised with regard to the filter coefficients. The filter will then make the filter output y(k) approximately equal to the signal disturbance n(k).

If several disturbances add up, a reference signal may be configured to correlate with the sum of the disturbances, or else a plurality of adaptive filters may be used in series, removing each disturbance in rotation. Before the reference signal continues to the filter, the amplitude and frequency content are adapted in 16 in accordance with the expected disturbance of the system in question, by removing the DC component and setting the mean amplitude of the reference signal 13 to a value approximately equal to half of the amplitude of the primary signal 10. The output signal then goes directly to the VF algorithm if the system is integrated into a defibrillator 26 (FIGS. 5a, 5b, 5c), or to signal outlet 5 (FIG. 1).

If the filter solution is not too complex relative to the processor capacity of the system, the best filter solution will be achieved by optimising the filter coefficient as a function of the Wiener solution, instead of an approximate solution obtained through using the Conjugate Gradient method for an approximate solution of the Wiener-Hopf equation.

Signal Outlet 5

Signal outlet 5 is of interest in applications in which the defibrillator 26 is a stand-alone unit. The output signal is converted from digital to analogue form, and is made available to an external defibrillator. It may also be of interest to include components that connect the defibrillator shocks to the patient via the same electrodes as those used by the ECG measuring system.

Figure 4:
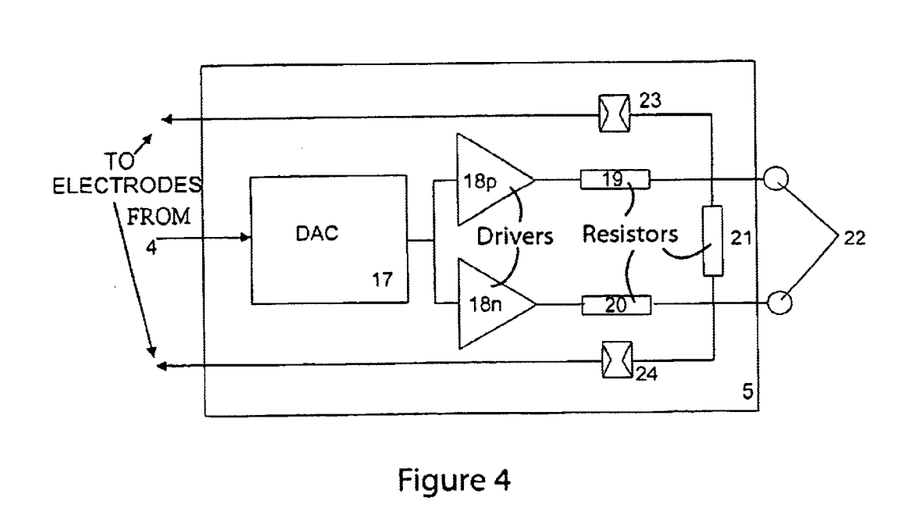
FIG. 4 shows the elementary diagram for connecting the output signal to an external defibrillator, and for connecting the defibrillator shock to the electrodes.

A solution for this is shown in FIG. 4, which shows an example of a basic circuit arrangement for the signal outlet. From the processor and filter system 4, the output signal 11 continues to a digital to analogue converter (DAC) 17, and from there to two drivers 18p, 18n, which output currents having a phase difference of 180°, and then on to a resistance network 19, 20, 21 that sets the amplitude and protects the drivers 18p, 18n. An external defibrillator will then be able to connect across the resistor 21 via terminals 22, and be able to measure an ECG in which the signal disturbances are reduced or completely eliminated. As the resistance of 21 is far greater than that of the body, most of the defibrillator shock will pass to the patient 25 via gas dischargers 23, 24.

Figure 6:
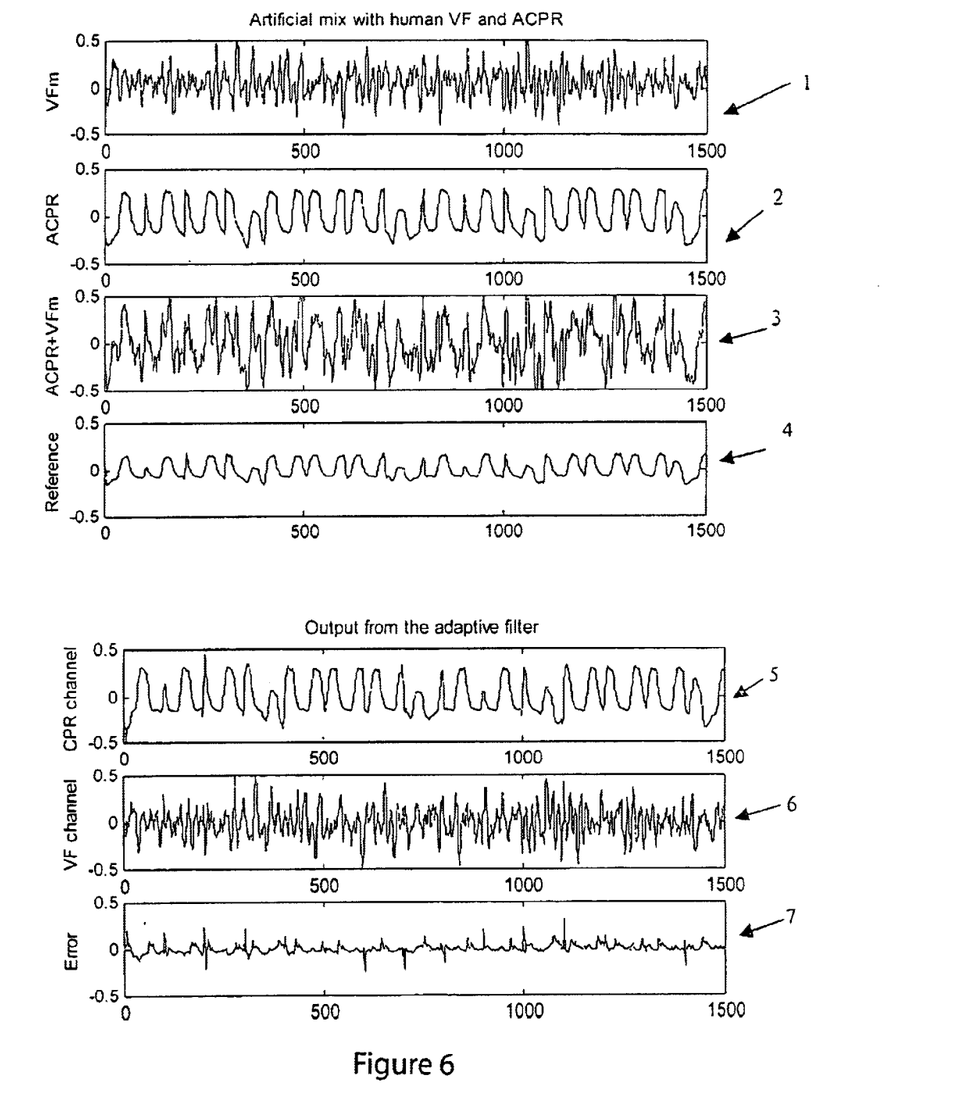
FIG. 6 shows an example of a signal sequence when using adaptive filtering, in which the signal disturbance is added to a clean VF signal and then filtered out through the use of adaptive filtering.

FIG. 6 shows an example of the sequence of signals when using adaptive filtering, where the signal disturbance is added to a clean VF signal and then filtered out through use of adaptive filtering:

Curve 1 in FIG. 6 shows VF from a person, VFm, here without signal disturbance.

Curve 2 in FIG. 6 shows signal disturbances during CPR, measured on a pig.

Curve 3 in FIG. 6 shows the sum of signals 1 and 2, and represents a VF disturbed by CPR. This is the primary signal d(k).

Curve 4 in FIG. 6 shows the reference signal r(k), which is made up of the signal from the position transducer and from the impedance measuring system.

Curve 5 in FIG. 6 shows the output yl(k), which expresses the signal disturbance estimated by the filter.

Curve 6 in FIG. 6 shows the output e(k), which expresses the VF signal e(k) estimated by the filter.

Curve 7 in FIG. 6 shows the difference between the initial signal VFm and e(k), which also represents the error in the estimated signal.

Applications

The system may be used as an integrated part of a defibrillator, cf. FIG. 5a, and will in this case be able to make use of components and solutions that are already a part of this; typically the ECG measuring system, the ADC, and the processor system. In addition to the adaptive digital filter, such a solution will also require a representative reference measuring system. In this case, the signal outlet will not be put to use, as the defibrillator uses a filtered ECG in a digital format.

A third attractive possibility is to connect the solution to an automatic CPR machine 28, cf. FIG. 5b. This type of equipment is in general use in many ambulance systems, and will be able to administer high quality CPR over an extended time. Because the CPR is automated, the defibrillator can deliver shocks simultaneously with the administration of the CPR, without the risk of exposing the lifesavers to high voltages. Thus there is no delay between the CPR and the shock delivery, a factor that is reported to increase the probability of ROSC.

Figure 5C:
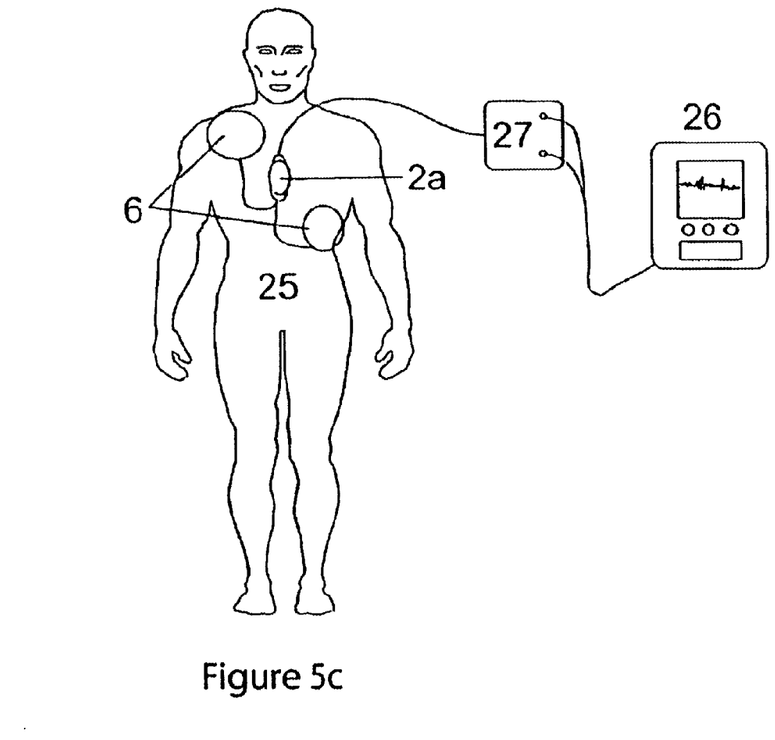
FIG. 5c shows an application where the system forms a self-contained unit, used with a defibrillator.

A stand-alone system will be an attractive application for many users, as this allows the use of existing defibrillators. This is illustrated in FIG. 5c. In this case, all the system components will be included.

What is claimed is:

1. A system for reducing signal disturbances in ECG of a patient, which disturbances are caused by cardio-pulmonary resuscitation (CPR), the system comprising:

a device for measuring ECG signals, a plurality of devices for measuring respective reference signals that arise as a function of CPR, where references signals represent measurements that are related to causes of signal disturbances in ECG, and a computational unit connected by separate inlets to receive respective reference and ECG signals, wherein the computational unit includes one or more digital adaptive filters which calculate an estimate of the signal disturbance as a function of the correlation between the signal disturbance caused by CPR and the reference signals to enable the computational unit to produce an output that represents the difference between the ECG signal and the estimated signal disturbance; and the plurality of devices for measuring respective reference signals that arise as a function of CPR comprise a device for measuring a reference signal by measuring an impedance change between two electrodes placed at standard defibrillation positions and a device for measuring another reference signal by estimating a current running between the patient and a ground of the device for measuring ECG signals.

2. A system according to claim 1, wherein the device for measuring a reference signal by measuring an impedance change measures a change of impedance in a chest during a chest compression.

3. A system according to claim 1, wherein the devices for measuring reference signals further comprise a device for measuring compression depth as a reference signal, including a linear position transmitter installed on an automatic CPR machine.

4. A system according to claim 1, wherein the devices for measuring reference signals further comprise a device for measuring compression depth as a reference signal, including a pressure sensor that reads the pressure that drives a piston in an automatic CPR machine.

5. A system according to claim 1, wherein the device for measuring a reference signal by measuring an impedance change measures a change of impedance in a chest during a lung inflation.

6. A system according to claim 1, wherein the devices for measuring reference signals further comprise a device for measuring lung inflation as a reference signal, including a pressure sensor that is connected to a patient's respiratory passage.

7. A system according to claim 1, wherein the devices for measuring reference signals further comprise a device for measuring lung inflation as a reference signal, including a flow meter connected to a respiratory passage going into and out of a patient.

8. A system according to claim 1, wherein the devices for measuring reference signals further comprise a device for measuring lung inflation as a reference signal, including a thermocouple that is actuated by air flowing into and out of a patient.

9. A system according to claim 1, wherein the device for measuring a reference signal by estimating the current includes a voltage meter connected to a resistor that is connected between an earth electrode running to the patient, and the ground of the ECG measuring device.

10. A system according to claim 1, wherein the device for estimating the current includes a voltage meter connected to a resistor that is connected to a point that represents a mid-point of a potential between electrodes and the ground of the ECG measuring device.

11. A system according to claim 1, wherein the system is integrated into a defibrillator.

12. A system according to claim 1, wherein the system forms a functional unit connected to an automatic CPR machine.

13. A system according to claim 1, wherein the system forms a self-contained unit that can be connected to a defibrillator.

14. A system according to claim 1, wherein at least one of the devices for measuring a reference signal measures compression depth as the reference signal, the at least one device including a signal processing unit that estimates the compression depth as a function of a signal reflecting acceleration of a patient's chest from an accelerometer designed to follow movements of the chest.

15. A system according to claim 1, wherein the impedance change represents a measurement that is related to a cause of a signal disturbance in ECG resulting from at least heart compression.

16. A system according to claim 1, wherein the impedance change represents a measurement that is related to a cause of a signal disturbance in ECG resulting from at least heart compression and lung inflation.

17. A system according to claim 1, wherein the estimated current represents a signal disturbance in ECG resulting from at least lung inflation.

18. A system according to claim 1, wherein the impedance change represents a measurement that is related to a cause of a signal disturbance in ECG resulting from at least heart compression; and the estimated current represents a signal disturbance in ECG resulting from at least lung inflation.

19. A system according to claim 1, wherein the impedance change represents a measurement that is related to a cause of a signal disturbance in ECG resulting from at least heart compression and lung inflation; and the estimated current represents a signal disturbance in ECG resulting from at least lung inflation.

* * * * *